United States Patent
Liu et al.

(10) Patent No.: US 10,258,929 B2
(45) Date of Patent: Apr. 16, 2019

(54) STABLE FACILITATED TRANSPORT MEMBRANES FOR OLEFIN/PARAFFIN SEPARATIONS

(71) Applicant: UOP LLC, Des Plaines, IL (US)

(72) Inventors: Chunqing Liu, Arlington Heights, IL (US); Nicole K. Karns, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 83 days.

(21) Appl. No.: 15/600,300

(22) Filed: May 19, 2017

(65) Prior Publication Data

US 2018/0001268 A1    Jan. 4, 2018

Related U.S. Application Data

(60) Provisional application No. 62/357,229, filed on Jun. 30, 2016.

(51) Int. Cl.
*B01D 53/00* (2006.01)
*B01D 67/00* (2006.01)
*B01D 69/10* (2006.01)
*B01D 69/14* (2006.01)
*C07C 7/144* (2006.01)
*C10G 45/32* (2006.01)
*B01D 53/22* (2006.01)
*B01D 69/02* (2006.01)
*B01D 71/64* (2006.01)
*B01D 71/68* (2006.01)

(52) U.S. Cl.
CPC ....... *B01D 67/0079* (2013.01); *B01D 53/228* (2013.01); *B01D 67/0002* (2013.01); *B01D 67/0088* (2013.01); *B01D 69/02* (2013.01); *B01D 69/10* (2013.01); *B01D 69/141* (2013.01); *B01D 69/142* (2013.01); *C07C 7/144* (2013.01); *C10G 45/32* (2013.01); *B01D 67/0011* (2013.01); *B01D 71/64* (2013.01); *B01D 71/68* (2013.01); *B01D 2325/023* (2013.01); *B01D 2325/04* (2013.01); *B01D 2325/20* (2013.01); *C10G 2400/08* (2013.01); *C10G 2400/20* (2013.01)

(58) Field of Classification Search
CPC .............. B01D 67/0088; B01D 71/68; B01D 2325/023; B01D 67/0011; B01D 69/142; B01D 71/64; B01D 2325/04; B01D 67/0002; B01D 67/0079; B01D 53/228; B01D 69/10; B01D 2325/20; B01D 69/141; B01D 69/02; C10G 45/32; C10G 2400/20; C10G 2400/08; C07C 7/144
See application file for complete search history.

(56) References Cited

U.S. PATENT DOCUMENTS

| | | | | |
|---|---|---|---|---|
| 4,800,162 A | * | 1/1989 | Matson | B01J 19/2475 435/135 |
| 5,196,568 A | * | 3/1993 | Zepp | B01J 19/2475 560/110 |
| 5,198,568 A | * | 3/1993 | Zepp | C12P 41/00 560/100 |
| 5,256,295 A | | 10/1993 | Baker et al. | |
| 5,670,051 A | | 9/1997 | Pinnau et al. | |
| 7,361,800 B2 | | 4/2008 | Herrera et al. | |
| 7,803,275 B2 | | 9/2010 | Partridge et al. | |
| 8,366,804 B2 | | 2/2013 | Liu et al. | |
| 8,561,812 B2 | | 10/2013 | Liu et al. | |
| 8,829,059 B2 | | 9/2014 | Wynn | |
| 8,912,288 B2 | | 12/2014 | Liu et al. | |
| 9,017,451 B2 | | 4/2015 | Wynn et al. | |
| 9,126,152 B2 | | 9/2015 | Liu et al. | |
| 9,126,154 B2 | | 9/2015 | Liu et al. | |
| 9,126,155 B2 | | 9/2015 | Liu et al. | |
| 9,126,156 B2 | | 9/2015 | Liu et al. | |
| 9,211,508 B2 | | 12/2015 | Liu et al. | |

(Continued)

FOREIGN PATENT DOCUMENTS

| EP | 458598 A2 | 11/1991 |
|---|---|---|
| EP | 1375459 A1 | 1/2004 |

OTHER PUBLICATIONS

Hess et. al., Propene/propane separation with copolyimide membranes containing silver ions, Journal of Membrane Science, vol. 275, Issue 1-2, Apr. 20, 2006, pp. 52-60.
Kudinov, "Separation characteristics of an ejector membrane-sorption hybrid system", Theoretical Foundations of Chemical Engineering, vol. 48, Issue 6, Dec. 2, 2014, pp. 832-836.
Wernerson, "Supersonic compressors for hydrogen recovery", Hydrocarbon Engineering, vol. 11, Issue 12, Dec. 2006, pp. 47-48.
Kang, "Novel Application of Partially Positively Charged Silver Nanoparticles for Facilitated Transport in Olefin/Paraffin Separation Membranes", Chem. Mater. 2008, 20, 1308-1311.

(Continued)

*Primary Examiner* — Anthony R Shumate

(57) ABSTRACT

A stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide and the asymmetric integrally-skinned polymeric membrane comprises a relatively porous, thin, dense skin layer as characterized by a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure. The present invention further includes a method of making these membranes and their use for olefin/paraffin separations, particularly for propylene/propane and ethylene/ethane separations.

13 Claims, No Drawings

(56) References Cited

U.S. PATENT DOCUMENTS

| | | | |
|---|---|---|---|
| 2006/0000778 A1* | 1/2006 | Childs | B01D 61/362 210/644 |
| 2010/0018926 A1 | 1/2010 | Liu et al. | |
| 2010/0147148 A1 | 6/2010 | Rabiei | |
| 2010/0226823 A1* | 9/2010 | Rakhman | B01D 53/268 422/84 |
| 2011/0091698 A1* | 4/2011 | Zhou | B01D 67/0006 428/212 |
| 2011/0094960 A1* | 4/2011 | Zhou | B01D 67/0006 210/500.27 |
| 2011/0316181 A1 | 12/2011 | Liu et al. | |
| 2012/0285881 A1* | 11/2012 | Jikihara | B01D 69/02 210/490 |
| 2013/0255483 A1 | 10/2013 | Sanders et al. | |
| 2014/0137734 A1 | 5/2014 | Liu et al. | |
| 2014/0290478 A1 | 10/2014 | Liu et al. | |
| 2015/0053079 A1 | 2/2015 | Koros et al. | |
| 2015/0098872 A1 | 4/2015 | Kelly et al. | |
| 2016/0177035 A1 | 6/2016 | Liu et al. | |
| 2016/0325229 A1* | 11/2016 | Zhou | B01D 61/362 |
| 2017/0291143 A1* | 10/2017 | Zhou | B01D 61/36 |
| 2018/0154311 A1* | 6/2018 | Zhou | B01D 61/362 |
| 2018/0229186 A1* | 8/2018 | Yandrasits | B01D 61/362 |

OTHER PUBLICATIONS

Search Report dated Oct. 5, 2017 for corresponding PCT Appl. No. PCT/US2017/038307.

* cited by examiner

US 10,258,929 B2

STABLE FACILITATED TRANSPORT MEMBRANES FOR OLEFIN/PARAFFIN SEPARATIONS

CROSS-REFERENCE TO RELATED APPLICATION

This application claims priority from Provisional Application No. 62/357,229 filed Jun. 30, 2016, the contents of which cited application are hereby incorporated by reference in its entirety.

BACKGROUND OF THE INVENTION

Light olefins, such as propylene and ethylene, are produced as co-products from a variety of feed stocks in a number of different processes in the chemical, petrochemical, and petroleum refining industries. Various petrochemical streams contain olefins and other saturated hydrocarbons. Typically, these streams are from stream cracking units (ethylene production), catalytic cracking units (motor gasoline production), or the dehydrogenation of paraffins.

Currently, the separation of olefin and paraffin components is performed by cryogenic distillation, which is expensive and energy intensive due to the low relative volatilities of the components. Large capital expense and energy costs have created incentives for extensive research in this area of separations, and low energy-intensive membrane separations have been considered as an attractive alternative.

In principle, membrane-based technologies have advantages of both low capital cost and high-energy efficiency compared to conventional separation methods for olefin/paraffin separations, such as propylene/propane and ethylene/ethane separations. Four main types of membranes have been reported for olefin/paraffin separations including facilitated transport membranes, polymer membranes, mixed matrix membranes, and inorganic membranes. Facilitated transport membranes, or ion exchange membranes, which sometimes use silver ions as a complexing agent, have very high olefin/paraffin separation selectivity. However, poor chemical stability due to carrier poisoning or loss, high cost, and low flux currently limit practical applications of facilitated transport membranes.

Separation of olefins from paraffins via conventional polymer membranes has not been commercially successful due to inadequate selectivities and permeabilities of the polymeric membrane materials, as well as plasticization issues. Polymers that are more permeable are generally less selective than are less permeable polymers. A general trade-off exists between permeability and selectivity of the polymeric membrane materials (the so-called "polymer upper bound limit") for all kinds of separations, including olefin/paraffin separations. In recent years, substantial research effort has been directed to overcoming the limits imposed by this upper bound. Various polymers and techniques have been used, but without much success in terms of improving the membrane selectivity.

Much more efforts have been undertaken to develop metal ion incorporated, high olefin/paraffin selectivity facilitated transport membranes. The high selectivity for olefin/paraffin is achieved by the incorporation of metal ions such as silver (I) and copper (I) cations into a solid nonporous polymer matrix layer on top of a highly porous membrane support layer (so-called "fixed site carrier facilitated transport membrane") or directly into the pores of the highly porous support membrane (so-called "supported liquid facilitated transport membrane") that results in the formation of a reversible metal cation complex with the pi bond of olefins, whereas no interaction occurs between the metal cations and the paraffins. Addition of water, plasticizer, or humidification of the olefin/paraffin feed streams to either the fixed site carrier facilitated transport membranes or the supported liquid facilitated transport membranes is usually required to obtain reasonable olefin permeances and high olefin/paraffin selectivities. The performance of fixed site carrier facilitated transport membranes is much more stable than that of the supported liquid facilitated transport membranes. The fixed site carrier facilitated transport membranes are less sensitive to the loss of metal cation carriers than the supported liquid facilitated transport membranes.

Pinnau et al. disclosed a solid polymer electrolyte fixed site carrier facilitated transport membrane comprising silver tetrafluoroborate incorporated poly(ethylene oxide), see U.S. Pat. No. 5,670,051. Herrera et al. disclosed a process for the separation of olefin/paraffin using a silver cation-chelated chitosan fixed site carrier facilitated transport membrane, see U.S. Pat. No. 7,361,800. Herrera et al. reported the coating of a layer of chitosan on the surface of a support membrane, wherein the support membrane is made from polyesters, polyamides, polyimides, polyvinylidene fluoride, polyacrylonitrile, polysulphones or polycarbonates. Common composite facilitated transport membranes comprise ultrafiltration or microfiltration membrane as the support membrane.

Feiring et al. disclosed a new facilitated transport membrane comprising silver (I) cation exchanged fluorinated copolymer synthesized from a perfluorinated cyclic or cyclizable monomer and a strong acid highly fluorinated vinylether compound. The membrane, however, did not show olefin to paraffin selectivity higher than 200, see US 2015/0025293.

The composite facilitated transport membranes disclosed in the literature comprise an ultrafiltration or microfiltration membrane as the support membrane. The use of a relatively hydrophilic, nanoporous polymeric membrane such as polyethersulfone membrane as the support membrane for the preparation of fixed site carrier facilitated transport membranes for olefin/paraffin separations has not been reported in the literature. In particular, the use of a relatively hydrophilic, very small pore, nanoporous support membranes with an average pore diameter of less than 10 nm on the membrane skin layer surface for the preparation of fixed site carrier facilitated transport membranes has not been disclosed in the literature.

Development of new stable, high permeance, and high selectivity facilitated transport membranes is critical for the future success in the use of membranes for olefin/paraffin separations such as propylene/propane separation.

SUMMARY OF THE INVENTION

This invention discloses a new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide, wherein said asymmetric integrally-skinned polymeric membrane comprises a relatively porous, thin, dense skin layer as characterized by a carbon dioxide ($CO_2$) permeance of at least 200 GPU and a $CO_2$ over methane ($CH_4$) selectivity between 1.1 and 10 at 50° C. under 50-1000 psig, 10% $CO_2$/90% $CH_4$ mixed gas feed pressure.

The asymmetric integrally-skinned polymeric membranes wherein the pores on the relatively porous, thin, dense skin layer of the membrane comprises a hydrophilic polymer such as chitosan or sodium alginate in the present invention is required to have a $CO_2$ permeance of at least 100 GPU and a $CO_2$ over $CH_4$ selectivity between 1.5 and 15 at 50° C. under 500-1000 psig, 10% $CO_2$/90% $CH_4$ mixed gas feed pressure. The present invention also discloses a method of making such a membrane, and the use of such a membrane for olefin/paraffin separations, particularly for propylene/propane (C3=/C3) and ethylene/ethane (C2=/C2) separations.

The current invention discloses a new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide. The present invention teaches the use of an asymmetric integrally-skinned polymeric membrane comprising a relatively porous, thin, dense skin layer as characterized by a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure for the preparation of the new facilitated transport membrane for olefin/paraffin separation. Preferably, the asymmetric integrally-skinned polymeric membrane comprising a relatively porous, thin, dense skin layer in the present invention is fabricated from a polyimide, a blend of two or more different polyimides, or a blend of a polyimide and a polyethersulfone. The present invention further teaches the use of a hydrophilic polymer such as chitosan, hyaluronic acid, or sodium alginate to nip the relatively porous, thin, dense skin layer of the asymmetric integrally-skinned polymeric membrane which has a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure. The hydrophilic polymer-nipped asymmetric integrally-skinned polymeric membrane in the present invention comprising hydrophilic polymers such as chitosan, hyaluronic acid, or sodium alginate inside the very small pores on the relatively porous, thin, dense skin layer of the membrane has a $CO_2$ permeance of at least 100 GPU and a $CO_2$ over $CH_4$ selectivity between 1.5 and 15 at 50° C. under 500-1000 psig, 10% $CO_2$/90% $CH_4$ mixed gas feed pressure.

The use of the asymmetric integrally-skinned polymeric membrane comprising a relatively porous, thin, dense skin layer and having a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure in the present invention and the incorporation of the hydrophilic polymer such as chitosan, hyaluronic acid, or sodium alginate inside the very small pores on the relatively porous, thin, dense skin layer of said membrane can fix and stablize the metal cations such as silver (I) cation inside the very small pores to prevent the loss of the metal cations from the membrane under the applied feed pressure. Therefore, the new facilitated transport membranes described in the present invention have shown high olefin/paraffin selectivity and very stable performance for olefin/paraffin separations.

The present invention also teaches a method for the preparation of the new stable high performance facilitated transport membrane for olefin/paraffin separation. Preferably, an aqueous hydrophilic polymer solution is used to nip the surface of the relatively porous, thin, dense skin layer of the asymmetric integrally-skinned polymeric membrane to incorporate the hydrophilic polymer such as chitosan, hyaluronic acid, or sodium alginate into the very small pores on the relatively porous, thin, dense skin layer of the membrane. The asymmetric integrally-skinned polymeric membrane comprising a relatively porous, thin, dense skin layer in the present invention is fabricated from a polyimide blend of two or more different polyimides, or a blend of a polyimide and a polyethersulfone. The hydrophilic polymer-nipped asymmetric integrally-skinned polymeric membrane with a relatively porous, thin, dense skin layer and wherein the very small pores on said skin layer comprises said hydrophilic polymer is then used as the support membrane for the preparation of the new stable high performance facilitated transport membrane.

The new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide described in the current invention showed high olefin/paraffin selectivity, high olefin permeance, and stable performance over time. The high selectivity and high permeance of the facilitated transport membranes described in the current invention is achieved by the use of an asymmetric integrally-skinned polymeric membrane wherein the pores on the relatively porous, thin, dense skin layer of the membrane comprises a hydrophilic polymer such as chitosan, hyaluronic acid, or sodium alginate as the support membrane to fix metal cations such as silver (I) cations inside the pores in the relatively porous, thin, dense skin layer of said membrane. The formation of a reversible metal cation complex with the pi bond of olefins, whereas no interaction occurs between the metal cations and the paraffins in the new facilitated transport membrane described in the present invention resulted in both high selectivity and high permeance for olefin/paraffin separations. The high stability of the facilitated transport membranes described in the current invention is achieved by the use of hydrophilic polymer-nipped asymmetric integrally-skinned polymeric membrane comprising a relatively porous, thin, dense skin layer and having a $CO_2$ permeance of at least 100 GPU and a $CO_2$ over $CH_4$ selectivity between 1.5 and 15 at 50° C. under 500-1000 psig, 10% $CO_2$/90% $CH_4$ mixed gas feed pressure.

As an example, a new stable high performance facilitated transport membrane 1.5 MAg+/PI-5-2000 ppmC described in the present invention was prepared by in-situ nipping the relatively porous, thin, dense skin layer of an asymmetric integrally skinned poly(3,3',4,4'-diphenylsulfone tetracarboxylic dianhydride-3,3',5,5'-tetramethyl-4,4'-methylene dianiline) polyimide (abbreviated as PI-5) polyimide flat sheet membrane with a 2000 ppm chitosan aqueous solution during the membrane casting process. The 2000 ppm chitosan-nipped skin layer surface of the 2000 ppm chitosan-nipped PI-5 asymmetric integrally skinned flat sheet membrane was soaked in an aqueous solution of 1.5 M silver nitrate for a certain time. The asymmetric integrally skinned PI-5 polyimide flat sheet membrane before chitosan nipping has a relatively porous, thin, dense skin layer, a $CO_2$ permeance of 4076 GPU, and a $CO_2$ over $CH_4$ selectivity of 1.14 at 50° C. under 100 psig, 10% $CO_2$/90% $CH_4$ mixed gas feed pressure. The 2000 ppm chitosan-nipped asymmetric integrally skinned PI-5 polyimide flat sheet membrane has decreased pore size in the relatively porous, thin, dense skin layer and shows a $CO_2$ permeance of 442 GPU, and a $CO_2$ over $CH_4$ selectivity of 4.1 at 50° C. under 1000 psig, 10% $CO_2$/90% $CH_4$ mixed gas feed pressure. Permeation testing experiments using humidified propylene and propane mixed vapor phase feed showed that this 1.5 MAg+/PI-5-2000 ppmC facilitated transport membrane has both stable high propylene (C3=) permeance ($P_{C3=}/L$=87.6 A.U.) and high propylene/propane (C3=/C3) selectivity ($\alpha_{C3=/C3}$>1000) at 50° C. under 791 kPa (100 psig), 70% C3=/30% C3 mixed vapor feed pressure. The 1.5 MAg+/PI-5-2000 ppmC facilitated transport membrane also has stable high propylene (C3=) permeance ($P_{C3=}/L$=149 A.U.) and high propylene/propane (C3=/C3) selectivity ($\alpha_{C3=/C3}$=268) at 50° C. under 791 kPa (100 psig), 30% C3=/70% C3 mixed vapor feed pressure.

The present invention also discloses a method of making the new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide described in the current invention. The method comprises:

Preparation of an asymmetric integrally-skinned polymeric membrane comprising a relatively porous, thin, dense skin layer and having a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure;

Preparation of the hydrophilic polymer-nipped asymmetric integrally-skinned polymeric membrane using an in-situ nipping approach using the asymmetric integrally-skinned polymeric membrane prepared in step 1) by dripping an aqueous solution of a hydrophilic polymer with a concentration in a range of 50 ppm to 5000 ppm onto the surface of the asymmetric integrally-skinned polymeric wet membrane comprising a relatively porous, thin, dense skin layer;

Preparation of the facilitated transport membrane by soaking the skin layer surface of the hydrophilic polymer-nipped asymmetric integrally-skinned polymeric membrane prepared in step 2) in an aqueous solution of a metal salt such as silver nitrate ($AgNO_3$) with a concentration in a range of 0.5 M to 10 M, or in an aqueous solution of a metal salt such as silver nitrate and hydrogen peroxide for a certain time to form the facilitated transport membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide.

The present invention provides a process for separating olefin from a mixture of olefin and paraffin using the new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide described in the present invention, the process comprising: (a) providing a new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide described in the present invention which is permeable to said olefin; (b) contacting the humidified olefin/paraffin mixture feed on one side of said membrane described in the present invention to cause said olefin to permeate the membrane; and (c) removing from the opposite side of the membrane a permeate gas composition comprising a portion of said olefin which permeated through said membrane.

DETAILED DESCRIPTION OF THE INVENTION

Membrane technology has been of great interest for the separation of olefin/paraffin mixtures. However, despite significant research effort on olefin/paraffin separations by membrane technology, no commercial olefin/paraffin separation application using membranes has been reported.

The present invention discloses a new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide wherein said asymmetric integrally-skinned polymeric membrane comprises a relatively porous, thin, dense skin layer as characterized by a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure. The asymmetric integrally-skinned polymeric membranes wherein the pores on the relatively porous, thin, dense skin layer of the membrane comprises a hydrophilic polymer such as chitosan or sodium alginate in the present invention is required to have a $CO_2$ permeance of at least 100 GPU and a $CO_2$ over $CH_4$ selectivity between 1.5 and 15 at 50° C. under 500-1000 psig, 10% $CO_2$/90% $CH_4$ mixed gas feed pressure. The present invention further discloses a method of making such a membrane and the use of such a membrane for olefin/paraffin separations, particularly for propylene/propane (C3=/C3) and ethylene/ethane (C2=/C2) separations.

The new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide was prepared from an asymmetric integrally-skinned polymeric membrane comprising a relatively porous, thin, dense skin layer and having a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure. The asymmetric integrally-skinned polymeric membrane comprising a relatively porous, thin, dense skin layer described in the current invention was fabricated from a polymer selected from a group consisting of a polyimide, a blend of two or more different polyimides, or a blend of a polyimide and a polyethersulfone. The present invention further teaches the use of a hydrophilic polymer such as chitosan, hyaluronic acid, or sodium alginate to nip the relatively porous, thin, dense skin layer of the asymmetric integrally-skinned polymeric membrane which has a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure. The hydrophilic polymer-nipped asymmetric integrally-skinned polymeric membrane in the present invention comprising hydrophilic polymers such as chitosan, hyaluronic acid, or sodium alginate inside the very small pores on the relatively porous, thin, dense skin layer of the membrane has a $CO_2$ permeance of at least 100 GPU and a $CO_2$ over $CH_4$ selectivity between 1.5 and 15 at 50° C. under 500-1000 psig, 10% $CO_2$/90% $CH_4$ mixed gas feed pressure.

The polyimide used for the preparation the facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide in the current invention may be selected from, but is not limited to, the group consisting of poly(2,2'-bis-(3,4-dicarboxyphenyl)hexafluoropropane dianhydride-3,3',5,5'-tetramethyl-4,4'-methylene dianiline) polyimide derived from a polycondensation reaction of 2,2'-bis-(3,4-dicarboxyphenyl)hexafluoropropane dianhydride (6FDA) with 3,3',5,5'-tetramethyl-4,4'-methylene dianiline (TMMDA), poly(3,3',4,4'-diphenylsulfone tetracarboxylic dianhydride-3,3',5,5'-tetramethyl-4,4'-methylene dianiline) polyimide derived from the polycondensation reaction of 3,3',4,4'-diphenylsulfone tetracarboxylic dianhydride (DSDA) with TMMDA, poly(3,3',4,4'-benzophenone tetracarboxylic dianhydride-pyromellitic dianhydride-3,3',5,5'-tetramethyl-4,4'-methylene dianiline) polyimide derived from the polycondensation reaction of a mixture of 3,3',4,4'-benzophenone tetracarboxylic dianhydride (BTDA) and pyromellitic dianhydride (PMDA) with TMMDA and the molar ratio of BTDA to PMDA may be in a range of 2:1 to 1:2, poly(3,3',4,4'-benzophenone tetracarboxylic dianhydride-pyromellitic dianhydride-2,4,6-trimethyl-1,3-phenylenediamine) polyimide derived from the polycondensation reaction of a mixture of BTDA and PMDA with 2,4,6-trimethyl-1,3-phenylenediamine (TMPDA) and the molar ratio of BTDA to PMDA may be in a range of 2:1 to 1:2, poly(3,3',4,4'-benzophenone tetracarboxylic dianhydride-pyromellitic dianhydride-2,4,6-trimethyl-1,3-phenylenediamine-2,4-toluenediamine) polyimide derived from the polycondensation reaction of a mixture of BTDA and PMDA with a mixture of TMPDA and 2,4-toluenediamine (2,4-TDA) and the molar ratio of BTDA to PMDA may be in a range of 2:1 to 1:2 and the molar ratio of TMPDA to 2,4-TDA may be in a range of 5:1 to 1:5, poly(3,3',4,4'-diphenylsulfone tetracarboxylic dianhydride-3,3',5,5'-tetramethyl-4,4'-methylene dianiline-4,4'-diamino-2-methylazobenzene) polyimide derived from the polycondensation reaction of DSDA with a mixture of TMMDA and 4,4'-diamino-2-methylazobenzene (DAMAB) and the molar ratio of TMMDA to DAMAB may be in a range of 5:1 to 1:5, and blends thereof.

The present invention teaches the use of a hydrophilic polymer such as chitosan, hyaluronic acid, or sodium alginate to nip the relatively porous, thin, dense skin layer of an asymmetric integrally-skinned polymeric membrane which has a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure. The hydrophilic polymer such as chitosan, hyaluronic acid, or sodium alginate nipped asymmetric integrally-skinned polymeric membrane in the present invention comprises the hydrophilic polymer such as chitosan, hyaluronic acid, or sodium alginate inside the very small pores on the relatively porous, thin, dense skin layer of the asymmetric integrally-skinned polymeric membrane. The hydrophilic polymer such as chitosan, hyaluronic acid, or sodium alginate nipped asymmetric integrally-skinned polymeric membrane in the present invention has a $CO_2$ permeance of at least 100 GPU and a $CO_2$ over $CH_4$ selectivity between 1.5 and 15 at 50° C. under 500-1000 psig, 10% $CO_2$/90% $CH_4$ mixed gas feed pressure. The use of the asymmetric integrally-skinned polymeric membrane comprising a relatively porous, thin, dense skin layer and having a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure in the present invention and the incorporation of the hydrophilic polymer such as chitosan, hyaluronic acid, or sodium alginate inside the very small pores on the relatively porous, thin, dense skin layer of said membrane can fix and stablize the metal cations such as silver (I) cation inside the very small pores to prevent the loss of the metal cations from the membrane under the applied feed pressure. Therefore, the new facilitated transport membranes described in the present invention have shown high olefin/paraffin selectivity and very stable performance for olefin/paraffin separations.

The hydrophilic polymer is used as the nipping material for the preparation of the new stable facilitated transport membrane comprising an asymmetric integrally-skinned polymeric membrane wherein the pores on the relatively porous, thin, dense skin layer of the membrane comprise a hydrophilic polymer such as chitosan or sodium alginate, a metal salt such as silver nitrate or a mixture of a metal salt such as silver nitrate and hydrogen peroxide in the present invention. The preferred hydrophilic polymers described in the present invention, but are not limited to, can be selected from a group of polymers containing chitosan, sodium carboxylmethyl-chitosan, carboxylmethyl-chitosan, hyaluronic acid, carbopol, polycarbophil calcium, poly(acrylic acid) (PAA), poly(methacrylic acid) (PMA), sodium alginate, alginic acid, poly(vinyl alcohol) (PVA), poly(ethylene oxide) (PEO), poly(ethylene glycol) (PEG), poly(vinylpyrrolidone) (PVP), gelatin, carrageenan, sodium lignosulfonate, and mixtures thereof.

The present invention also discloses a method of making the new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide described in the current invention. The method comprises:

Preparation of an asymmetric integrally-skinned polymeric membrane comprising a relatively porous, thin, dense skin layer and having a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure. Preparation of the hydrophilic polymer-nipped asymmetric integrally-skinned polymeric membrane is by using an in-situ nipping approach using the asymmetric integrally-skinned polymeric membrane prepared in step 1) by dripping an aqueous solution of a hydrophilic polymer with a concentration in a range of 50 ppm to 5000 ppm onto the surface of the asymmetric integrally-skinned polymeric wet membrane comprising a relatively porous, thin, dense skin layer. Preparation of the facilitated transport membrane is by soaking the skin layer surface of the hydrophilic polymer-nipped asymmetric integrally-skinned polymeric membrane prepared in step 2) in an aqueous solution of a metal salt such as silver nitrate ($AgNO_3$) with a concentration in a range of 0.5 M to 10 M, or in an aqueous solution of a metal salt such as silver nitrate and hydrogen peroxide for a certain time to form the facilitated transport membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide.

The new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide described in the present invention can be fabricated into any convenient form suitable for a desired application. For example, the membranes can be in the form of hollow fibers, tubes, flat sheets, and the like. The form of the membrane may depend upon the nature of the membrane itself and the ease of manufacturing the form. The membrane can be assembled in a separator in any suitable configuration for the form of the membrane and the separator may provide for co-current, counter-current, or cross-current flows of the feed on the retentate and permeate sides of the membrane. In one exemplary embodiment a stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide in a spiral wound module is in the form of flat sheet having a thickness from about 30 to about 400 µm. In another exemplary embodiment a stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide is in a hollow fiber module that is in the form of thousands, tens of thousands, hundreds of thousands, or more, of parallel, closely-packed hollow fibers or tubes. In one embodiment, each fiber has an outside diameter of from about 200 micrometers (µm) to about 700 millimeters (mm) and a wall thickness of from about 30 to about 200 µm. In operation, a feed contacts a first surface of the membrane, a permeate permeates the membrane and is removed therefrom, and a retentate, not having permeated the membrane, also is removed therefrom. In another embodiment, a stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide can be in the form of flat sheet having a thickness in the range of from about 30 to about 400 µm.

The present invention provides a process for the separation of paraffin and olefin, such as, for example, in gaseous streams produced from stream cracking, catalytic cracking, the dehydration of paraffins, and the like using the new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide described in the present invention, and the process comprises: (a) providing a new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide described in the present invention which is permeable to said olefin; (b) contacting the humidified olefin/paraffin mixture feed on one side of the new stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide described in the present invention to cause said olefin to permeate the membrane; and (c) removing from the opposite side of the membrane a permeate gas composition comprising a portion of said olefin which permeated through said membrane. The process utilizes a stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide described in the present invention that is highly permeable but also highly selective to olefin, thus permitting olefin to permeate the membrane at a much higher rate than the paraffin. The membrane can take a variety of forms suitable for a particular application. For example, the membrane can be in the form of a flat sheet, hollow tube or fiber, and the like. In this regard, various embodiments of the process contemplated herein can be used to replace C2 and C3 splitters, as hybrid membrane distillation units for olefin purification, for recovery of olefins from polypropylene vent streams or from fluid catalytic cracking (FCC) off-gas streams, or the like. The process can also be used for the production of polymer grade propylene, thus offering significant energy, capital, and operating cost savings compared to conventional distillation.

The olefin/paraffin separation process using the stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide starts by contacting a first surface of the membrane with an olefin/paraffin feed. The olefin may comprise, for example, propylene or ethylene and the paraffin may comprise propane or ethane, respectively. The olefin/paraffin feed comprises a first concentration of olefin and a first concentration of paraffin depending on the application for which the membrane separation is used. For example, a propane dehydrogenation process typically provides a feed containing about 35 mass percent propylene, whereas a feed from an FCC unit generally contains about 75 mass percent propylene. The flow rate and temperature of the olefin/paraffin feed have those values that are suitable for a desired application. Next, a permeate is caused to flow through the membrane and from a second surface of the membrane. Because the stable high performance facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate, or a mixture of a metal salt such as silver nitrate and hydrogen peroxide for olefin/paraffin separations is much more selective to the olefin than to the paraffin, the permeate has a concentration of olefin that is higher than the concentration of the olefin in the feed. In one exemplary embodiment, the concentration of the olefin in the permeate is 99.5 mass percent. In addition, while some paraffin may permeate through the membrane, the permeate has a concentration of paraffin that is less than the concentration of the paraffin in the feed. The permeate can then be removed from the second surface of the membrane. As the permeate passes through the membrane, a retentate or residue, which has not permeated the membrane, is removed from the first surface of the membrane. The retentate has a concentration of olefin that is lower than the concentration of olefin in the feed and lower than the concentration of the permeate. The retentate also has a concentration of paraffin that is higher than a concentration of paraffin that is in the feed.

EXAMPLES

The following examples are provided to illustrate one or more preferred embodiments of the invention, but are not limited embodiments thereof. Numerous variations can be made to the following examples that lie within the scope of the invention.

Example 1

Preparation of 1.5 MAg+/PI-5-2000 ppmC Facilitated Transport Membrane

1) Fabrication of Chitosan-Nipped Asymmetric Integrally Skinned PI-5 Membrane

A PI-5 membrane casting dope containing poly(3,3',4,4'-diphenylsulfone tetracarboxylic dianhydride-3,3',5,5'-tetramethyl-4,4'-methylene dianiline) polyimide (abbreviated as PI-5), NMP, 1,3-dioxolane, tert-butanol, acetone, and n-octane was cast on a highly porous non-selective symmetric woven Nylon 6,6 fabric backing at a casting speed of 6 fpm at room temperature. The cast membrane was evaporated for 13 seconds to form the nascent asymmetric integrally-skinned flat sheet PI-5 membrane. The membrane was immersed into a cold water coagulation tank and then immersed into a hot water tank to remove the trace amount of organic solvents in the membrane. A 2000 ppm aqueous solution of chitosan was dripped onto the surface of the relatively porous and substantial void-containing asymmetric integrally skinned PI-5 wet membrane to form chitosan-nipped asymmetric PI-5 wet membrane (abbreviated as PI-5-2000 ppmC). Finally the wet membrane was wound up on a core roll. The aqueous chitosan solution concentration can be in a range of 50 ppm to 5000 ppm for the preparation of chitosan nipped PI-5 membranes with different amount of chitosan inside the pores in the skin layer of the PI-5 membrane.

2) Preparation of 1.5 MAg+/PI-5-2000 ppmC Facilitated Transport Membrane

The chitosan-nipped skin layer surface of the wet PI-5-2000 ppmC membrane was immersed in a 1.5 M $AgNO_3$ aqueous solution for 3 h and then the $AgNO_3$ aqueous solution was removed from the membrane surface to form 1.5 MAg+/PI-5-2000 ppmC facilitated transport membrane. The metal salt such as silver nitrate ($AgNO_3$) concentration in the aqueous solution can be varied from 0.5M to 10M to make the present facilitated transport membranes with different amount of metal salt inside the pores in the skin layer of the membrane.

Example 2

Preparation of 3 MAg+-$H_2O_2$/PI-5-2000 ppmC Facilitated Transport Membrane

1) Fabrication of Chitosan-Nipped Asymmetric Integrally Skinned PI-5 Membrane

The chitosan-nipped asymmetric integrally skinned PI-5 membrane was prepared using a procedure same as that described in Example 1.

2) Preparation of 3 MAg+-$H_2O_2$/PI-5-2000 ppmC Facilitated Transport Membrane

The chitosan-nipped skin layer surface of the wet PI-5-2000 ppmC membrane was immersed in an aqueous solution containing 3.0 M $AgNO_3$ and 1 wt % hydrogen peroxide ($H_2O_2$) for 2.5 h and then the $AgNO_3$ aqueous solution was removed from the membrane surface to form 3 MAg+-$H_2O_2$/PI-5-2000 ppmC facilitated transport membrane. The metal salt such as silver nitrate ($AgNO_3$) concentration in the aqueous solution can be varied from 0.5M to 10M and the $H_2O_2$ concentration in the aqueous solution can be varied from 0.1 wt % to 2 wt % to make the present facilitated transport membranes with different amount of metal salt inside the pores in the skin layer of the membrane.

Example 3

Preparation of 1.5 MAg+/PI-46-3000 Ppm a Facilitated Transport Membranes

1) Fabrication of Chitosan-Nipped Asymmetric Integrally Skinned PI-46 Membranes

A PI-46 membrane casting dope comprising poly(3,3',4,4'-benzophenone tetracarboxylic dianhydride-pyromellitic dianhydride-3,3',5,5'-tetramethyl-4,4'-methylene dianiline) polyimide with a molar ratio of BTDA to PMDA of 1:1 (abbreviated as PI-46), NMP, 1,3-dioxolane, isopropanol, acetone, and n-octane was cast on a highly porous non-selective symmetric woven Nylon 6,6 fabric backing at a casting speed of 6 fpm at room temperature. The cast membrane was evaporated for 13 seconds to form the nascent asymmetric integrally-skinned flat sheet PI-46 membrane. The membrane was immersed into a cold water coagulation tank and then immersed into a hot water tank to remove the trace amount of organic solvents in the membrane. A 3000 ppm aqueous solution of sodium alginate was dripped onto the surface of the relatively porous and substantial void-containing asymmetric integrally skinned PI-46 wet membrane to form sodium alginate-nipped asymmetric PI-46 wet membrane (abbreviated as PI-46-3000 ppmA). Finally the wet membrane was wound up on a core roll. The aqueous chitosan solution concentration can be in a range of 50 ppm to 5000 ppm for the preparation of sodium alginate nipped PI-46 membranes with different amount of sodium alginate inside the pores in the skin layer of the PI-46 membrane.

2) Preparation of 1.5 MAg+/PI-46-3000 ppmA Facilitated Transport Membrane

The chitosan-nipped skin layer surface of the wet PI-46-3000 ppmA membrane was immersed in a 1.5M $AgNO_3$ aqueous solution for 2.5 h and then the $AgNO_3$ aqueous solution was removed from the membrane surface to form 1.5 MAg+/PI-46-3000 ppmA facilitated transport membrane. The metal salt such as silver nitrate ($AgNO_3$) concentration in the aqueous solution can be varied from 0.5M to 10M to make the present facilitated transport membranes with different amount of metal salt inside the pores in the skin layer of the membrane.

Example 4

Preparation of 1.5 MAg+-$H_2O_2$/PI-46-3000 ppmA Facilitated Transport Membrane

1) Fabrication of Chitosan-Nipped Asymmetric Integrally Skinned PI-46 Membrane

The chitosan-nipped asymmetric integrally skinned PI-46 membrane was prepared using a procedure same as that described in Example 3.

2) Preparation of 1.5 MAg+-$H_2O_2$/PI-46-3000 ppmA Facilitated Transport Membrane The sodium alginate-nipped skin layer surface of the wet PI-46-3000 ppmA membrane was immersed in an aqueous solution containing 1.5 M $AgNO_3$ and 1 wt % hydrogen peroxide ($H_2O_2$) for 2.5 h and then the $AgNO_3$ aqueous solution was removed from the membrane surface to form 1.5 MAg+-$H_2O_2$/PI-46-3000 ppmA facilitated transport membrane. The metal salt such as silver nitrate ($AgNO_3$) concentration in the aqueous solution can be varied from 0.5M to 10M and the $H_2O_2$ concentration in the aqueous solution can be varied from 0.1 wt % to 2 wt % to make the present facilitated transport membranes with different amount of metal salt inside the pores in the skin layer of the membrane.

Example 5

Preparation of 3 MAg+/PI-5-PES-2000 ppmC Facilitated Transport Membrane

1) Fabrication of Chitosan-Nipped Asymmetric Integrally Skinned PI-5-PES Membrane A PI-5-PES blend membrane casting dope comprising PI-5, polyethersulfone (PES), NMP, 1,3-dioxolane, tert-butanol, acetone, and n-octane with PI-5 to PES weight ratio of 1:1 was cast on a highly porous non-selective symmetric woven Nylon 6,6 fabric backing at a casting speed of 6 fpm at room temperature. The cast membrane was evaporated for 13 seconds to form the nascent asymmetric integrally-skinned flat sheet PI-5-PES membrane. The membrane was immersed into a cold water coagulation tank and then immersed into a hot water tank to remove the trace amount of organic solvents in the membrane. A 2000 ppm aqueous solution of chitosan was dripped onto the surface of the relatively porous and substantial void-containing asymmetric integrally skinned PI-5-PES wet membrane to form chitosan-nipped asymmetric PI-5-PES wet membrane (abbreviated as PI-5-PES-2000 ppmC). Finally the wet membrane was wound up on a core roll. The aqueous chitosan solution concentration can be in a range of 50 ppm to 5000 ppm for the preparation of chitosan nipped PI-5-PES membranes with different amount of chitosan inside the pores in the skin layer of the PI-5-PES membrane.

2) Preparation of 3 MAg+/PI-5-PES-2000 ppmC Facilitated Transport Membrane

The chitosan-nipped skin layer surface of the wet PI-5-PES-2000 ppmC membrane was immersed in a 3M $AgNO_3$ aqueous solution for 2.5 h and then the $AgNO_3$ aqueous solution was removed from the membrane surface to form 3 MAg+/PI-5-PES-2000 ppmC facilitated transport membrane. The metal salt such as silver nitrate ($AgNO_3$) concentration in the aqueous solution can be varied from 0.5M to 10M to make the present facilitated transport membranes with different amount of metal salt inside the pores in the skin layer of the membrane.

Comparative Example 1

Preparation of 3 MAg+/PI-5 Facilitated Transport Membrane

1) Fabrication of Asymmetric Integrally Skinned PI-5 Membrane

A PI-5 membrane casting dope comprising PI-5, NMP, 1,3-dioxolane, glycerol, and n-decane was cast on a highly porous non-selective symmetric woven Nylon 6,6 fabric backing at a casting speed of 6 fpm at room temperature. The cast membrane was evaporated for 13 seconds to form the nascent asymmetric integrally-skinned flat sheet PI-5 membrane. The membrane was immersed into a cold water coagulation tank and then immersed into a hot water tank to remove the trace amount of organic solvents in the membrane. Finally the wet membrane was wound up on a core roll.

2) Preparation of 3 MAg+/PI-5 Facilitated Transport Membrane

The skin layer surface of the wet PI-5 membrane was immersed in a 3M $AgNO_3$ aqueous solution for 2.5 h and then the $AgNO_3$ aqueous solution was removed from the membrane surface to form 3 MAg+/PI-5 facilitated transport membrane.

Example 6

$CO_2$/$CH_4$ Separation Performance of Dried PI-5, PI-5-2000 ppmC, and PI-46-3000 ppmA Asymmetric Integrally-Skinned Flat Sheet Membranes To control the pore size in the relatively porous, thin, dense skin layer of the asymmetric integrally-skinned polymeric membranes for the preparation of the stable high selectivity facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate or a mixture of a metal salt such as silver nitrate and hydrogen peroxide in the present invention, the asymmetric integrally-skinned polymeric membranes in the current invention is required to have a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure. The hydrophilic polymer-nipped asymmetric integrally-skinned polymeric membranes for the preparation of the stable high selectivity facilitated transport membrane comprising an asymmetric integrally-skinned polymeric membrane wherein the pores on the relatively porous, thin, dense skin layer of the membrane comprises a hydrophilic polymer such as chitosan or sodium alginate, a metal salt such as silver nitrate or a mixture of a metal salt such as silver nitrate and hydrogen peroxide in the present invention is required to have a $CO_2$ permeance of at least 100 GPU and a $CO_2$ over $CH_4$ selectivity between 1.5 and 15 at 50° C. under 500-1000 psig, 10% $CO_2$/90% $CH_4$ mixed gas feed pressure.

Dried PI-5, PI-5-2000 ppmC, and PI-46-3000 ppmA asymmetric integrally-skinned flat sheet membranes were tested using a 10% $CO_2$/90% $CH_4$ mixed gas at 50° C. under 791-3549 kPa (100-500 psig) feed pressure. The results in Table 1 show that PI-5 asymmetric integrally-skinned flat sheet membrane disclosed in the present invention has shown high $CO_2$ permeance of 851 GPU and $CO_2/CH_4$ selectivity of 1.8 at 50° C. under 3549 kPa, 10% $CO_2$/90% $CH_4$ mixed gas feed pressure. The chitosan-nipped PI-5-2000 ppmC asymmetric integrally-skinned flat sheet membrane has shown increased $CO_2/CH_4$ selectivity and decreased $CO_2$ permeance, suggesting that the chitosan-nipped PI-5-2000 ppmC asymmetric integrally-skinned flat sheet membrane has reduced pore size in the relatively porous, thin, dense skin layer of the membrane compared to the original PI-5 asymmetric integrally-skinned flat sheet membrane. The desired very small pores with reduced pore size will improve the fixation and stabilization the metal cations such as silver cations in the pores of the membranes. Table 1 also shows that the sodium alginate-nipped PI-46-3000 ppmA asymmetric integrally-skinned flat sheet membrane comprising sodium alginate polymer inside the very small pores on the relatively porous, thin, dense skin layer of the membrane has $CO_2$ permeance of 133 GPU and $CO_2/CH_4$ selectivity of 12.9 at 50° C. under 6996 kPa, 10% $CO_2$/90% $CH_4$ mixed gas feed pressure.

TABLE 1

$CO_2/CH_4$ permeation test results of PI-5, PI-5-2000 ppmC, and PI-46-3000 ppmA membranes

| Membrane | $P_{CO2}/L$ (GPU) | $\alpha_{CO2/CH4}$ |
|---|---|---|
| PI-5 [a] | 851 | 1.8 |
| PI-5-2000 ppmC [b] | 442 | 4.1 |
| PI-46-3000 ppmA [b] | 133 | 12.9 |

[a] Tested at 50° C., 10% $CO_2$/90% $CH_4$, 3549 kPa (500 psig) feed pressure;
[b] Tested at 50° C., 10% $CO_2$/90% $CH_4$, 6996 kPa (1000 psig) feed pressure; 1 GPU = $10^{-6}$ cm$^3$(STP)/cm$^2$ s (cm Hg).

Example 7

Evaluation of Propylene/Propane Separation Performance of 3 MAg+/PI-5, 1.5 MAg+/PI-5-2000 ppmC, 3 MAg+/PI-5-2000 ppmC, and 1.5 MAg+/PI-46-3000 ppmA Facilitated Transport Membranes The 3 MAg+/PI-5, 1.5 MAg+/PI-5-2000 ppmC, and 3 MAg+/PI-5-2000 ppmC facilitated transport membranes were evaluated for propylene/propane separation at 50° C. under 791 kPa (100 psig) propylene/propane (70%/30% or 30%/70%) mixed vapor phase feed pressure wherein the feed stream was bubbled through water at 50° C. The retentate flow rate was set at 708 scc/min. The results in Table 2 show that the new 3 MAg+/PI-5-2000 ppmC facilitated transport membrane prepared from chitosan-nipped PI-5-2000 ppmC asymmetric integrally-skinned flat sheet membrane disclosed in the present invention has high propylene/propane (C3=/C3) selectivity of >1000 and propylene (C3=) permeance of 87 GPU. However, the 3 MAg+/PI-5 facilitated transport membrane prepared from the original PI-5 asymmetric integrally-skinned flat sheet membrane without chitosan nipping showed low propylene/propane (C3=/C3) selectivity of 21.5.

The propylene/propane permeation experiments also demonstrated that the new 3 MAg+/PI-5-2000 ppmC facilitated transport membrane prepared from chitosan-nipped PI-5-2000 ppmC asymmetric integrally-skinned flat sheet membrane disclosed in the present invention showed stable membrane performance. As shown in Table 2, the membrane showed both stable propylene/propane (C3=/C3) selectivity and propylene (C3=) permeance after 6 h of continuous test.

TABLE 2

Propylene/propane permeation test results of 3MAg+/PI-5 and 3MAg+/PI-5-2000 ppmC facilitated transport membranes

| Membrane | $P_{C3=}/L$ (GPU) | $\alpha_{C3=/C3}$ |
|---|---|---|
| 3MAg+/PI-5 [a] | 109 | 21.5 |
| 3MAg+/PI-5-2000 ppmC [a] | 87 | >1000 |
| 3MAg+/PI-5-2000 ppmC [b] | 88 | >1000 |

Tested at 50° C., 791 kPa (100 psig) propylene/propane (70%/30%) mixed vapor feed pressure; feed stream was bubbled through water at 50° C.; retentate flow rate was set at 708 scc/min;
[a] data collected after 1 h of testing;
[b] data collected after 6 h of testing; 1 GPU = $10^{-6}$ cm$^3$ (STP)/cm$^2$ s (cm Hg).

The results in Table 3 show that the new 1.5 MAg+/PI-5-2000 ppmC and 3 MAg+/PI-5-2000 ppmC facilitated transport membranes prepared from chitosan-nipped PI-5-2000 ppmC asymmetric integrally-skinned flat sheet membrane and the new 1.5 MAg+/PI-46-3000 ppmA facilitated transport membrane prepared from sodium alginate-nipped PI-46-3000 ppmA asymmetric integrally-skinned flat sheet membrane disclosed in the present invention has high propylene/propane (C3=/C3) selectivities of >200 and propylene (C3=) permeances of 78-193 GPU with a 30%/70% propylene/propane mixed vapor phase feed. However, the 3 MAg+/PI-5 facilitated transport membrane prepared from the original PI-5 asymmetric integrally-skinned flat sheet membrane without chitosan nipping showed very low propylene/propane (C3=/C3) selectivity of 3.9.

TABLE 3

Propylene/propane permeation test results of 3MAg+/PI-5, 1.5MAg+/PI-5-2000 ppmC, 3MAg+/PI-5-2000 ppmC, and 1.5MAg+/PI-46-3000 ppmA facilitated transport membranes[a]

| Membrane | $P_{C3-}/L$ (GPU) | $\alpha_{C3-/C3}$ |
|---|---|---|
| 3MAg+/PI-5 | 148 | 3.9 |
| 3MAg+/PI-5-2000 ppmC | 78 | 203 |
| 1.5MAg+/PI-5-2000 ppmC | 149 | 268 |
| 1.5MAg+/PI-46-3000 ppmA | 193 | 315 |

[a]Tested at 50° C., 791 kPa (100 psig) propylene/propane (30%/70%) mixed vapor feed pressure; feed stream was bubbled through water at 50° C.; retentate flow rate was set at 708 scc/min; data collected after 1 h of testing; 1 GPU = $10^{-6}$ cm$^3$ (STP)/cm$^2$ s (cm Hg).

Specific Embodiments

While the following is described in conjunction with specific embodiments, it will be understood that this description is intended to illustrate and not limit the scope of the preceding description and the appended claims.

A first embodiment of the invention is a stable high performance facilitated transport membrane comprising an asymmetric integrally-skinned polymeric membrane wherein the pores on a relatively porous, thin, dense skin layer of the membrane comprises a hydrophilic polymer, a metal salt or a mixture of a metal salt and hydrogen peroxide, wherein the asymmetric integrally-skinned polymeric membrane comprises a relatively porous, thin, dense skin layer as characterized by a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure. The stable high performance facilitated transport membrane of the previous embodiments in this paragraph wherein the metal salt comprises silver nitrate. The stable high performance facilitated transport membrane of claim 1 comprising a polymer selected from a group consisting of a polyimide, a blend of two or more different polyimides, and a blend of a polyimide and a polyethersulfone. The stable high performance facilitated transport membrane of the previous embodiments in this paragraph wherein the polyimide is selected from the group consisting of poly(2,2'-bis-(3,4-dicarboxyphenyl)hexafluoropropane dianhydride-3,3',5,5'-tetramethyl-4,4'-methylene dianiline) polyimide derived from a polycondensation reaction of 2,2'-bis-(3,4-dicarboxyphenyl)hexafluoropropane dianhydride (6FDA) with 3,3',5,5'-tetramethyl-4,4'-methylene dianiline (TMMDA), poly(3,3',4,4'-diphenylsulfone tetracarboxylic dianhydride-3,3',5,5'-tetramethyl-4,4'-methylene dianiline) polyimide derived from the polycondensation reaction of 3,3',4,4'-diphenylsulfone tetracarboxylic dianhydride (DSDA) with TMMDA, poly(3,3',4,4'-benzophenone tetracarboxylic dianhydride-pyromellitic dianhydride-3,3',5, 5'-tetramethyl-4,4'-methylene dianiline) polyimide derived from the polycondensation reaction of a mixture of 3,3',4, 4'-benzophenone tetracarboxylic dianhydride (BTDA) and pyromellitic dianhydride (PMDA) with TMMDA, poly(3, 3',4,4'-benzophenone tetracarboxylic dianhydride-pyromellitic dianhydride-2,4,6-trimethyl-1,3-phenylenediamine) polyimide derived from the polycondensation reaction of a mixture of BTDA and PMDA with 2,4,6-trimethyl-1,3-phenylenediamine (TMPDA), poly(3,3',4,4'-benzophenone tetracarboxylic dianhydride-pyromellitic dianhydride-2,4,6-trimethyl-1,3-phenylenediamine-2,4-toluenediamine) polyimide derived from the polycondensation reaction of a mixture of BTDA and PMDA with a mixture of TMPDA and 2,4-toluenediamine (2,4-TDA), and poly(3,3',4,4'-diphenylsulfone tetracarboxylic dianhydride-3,3',5,5'-tetramethyl-4, 4'-methylene dianiline-4,4'-diamino-2-methylazobenzene) polyimide derived from the polycondensation reaction of DSDA with a mixture of TMMDA and 4,4'-diamino-2-methylazobenzene (DAMAB).

A second embodiment of the invention is a method of making a stable high performance facilitated transport membrane comprising an asymmetric integrally-skinned polymeric membrane wherein the method comprises: a) preparing an asymmetric integrally-skinned polymeric membrane comprising a relatively porous, thin, dense skin layer and having a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure; b) preparing a hydrophilic polymer-nipped asymmetric integrally-skinned polymeric membrane wherein the pores on the relatively porous, thin, dense skin layer of said asymmetric integrally-skinned polymeric membrane comprises a hydrophilic polymer such as chitosan or sodium alginate; c) preparing the facilitated transport membrane by soaking the hydrophilic polymer-nipped relatively porous, thin, dense skin layer of the hydrophilic polymer-nipped asymmetric integrally-skinned polymeric membrane prepared in step b) in an aqueous solution of a metal salt, or in an aqueous solution of a metal salt and hydrogen peroxide for a sufficient time to form the facilitated transport membrane wherein the relatively porous, thin, dense skin layer of the membrane comprises a hydrophilic polymer such as chitosan or sodium alginate, a metal salt, or a mixture of a metal salt and hydrogen peroxide. An embodiment of the invention is one, any or all of prior embodiments in this paragraph up through the first embodiment in this paragraph wherein the metal salt is silver nitrate. An embodiment of the invention is one, any or all of prior embodiments in this paragraph up through the first embodiment in this paragraph wherein the stable high performance facilitated transport membrane is in a form selected from the group consisting of hollow fibers, tubes and flat sheets. An embodiment of the invention is one, any or all of prior embodiments in this paragraph up through the first embodiment in this paragraph wherein the stable high performance facilitated transport membrane is in a form of a flat sheet having a thickness from about 30 to about 400 µm. An embodiment of the invention is one, any or all of prior embodiments in this paragraph up through the first embodiment in this paragraph wherein the stable high performance facilitated transport membrane is in a form of a hollow fiber module comprising from about 1,000 to 1,000, 000 parallel, hollow fibers or tubes wherein each hollow fiber has an outside diameter of from about 200 micrometers (µm) to about 700 millimeters (mm) and a wall thickness of from about 30 to about 200 µm.

A third embodiment of the invention is a process for the separation of paraffins and olefins, using a stable high performance facilitated transport membrane comprising an asymmetric integrally-skinned polymeric membrane wherein the pores on the relatively porous, thin, dense skin layer of the membrane comprises a hydrophilic polymer, a metal salt, or a mixture of a metal salt and hydrogen peroxide, the process comprising (a) providing a stable high performance facilitated transport membrane comprising an asymmetric integrally-skinned polymeric membrane wherein the pores on the relatively porous, thin, dense skin layer of the membrane comprises a hydrophilic polymer, a metal salt, or a mixture of a metal salt and hydrogen peroxide wherein the membrane is permeable to the olefin; (b) contacting a humidified olefin/paraffin mixture feed on one side of the said stable high performance facilitated transport membrane to cause the olefin to permeate the membrane; and (c) removing from the opposite side of said membrane a permeate gas composition comprising at least a portion of the olefin which permeated through the membrane. An embodiment of the invention is one, any or all of prior embodiments in this paragraph up through the second embodiment in this paragraph wherein the olefins and paraffins are in a gaseous stream produced from stream cracking, catalytic cracking, or the dehydration of paraffins. An embodiment of the invention is one, any or all of prior embodiments in this paragraph up through the second embodiment in this paragraph wherein the olefin comprises isobutylene, propylene or ethylene and the paraffin comprises isobutene, propane or ethane. An embodiment of the invention is one, any or all of prior embodiments in this paragraph up through the second embodiment in this paragraph wherein the permeate gas composition has a concentration of olefin of 99.5 mass percent.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A stable high performance facilitated transport membrane comprising an asymmetric integrally-skinned polymeric membrane wherein the pores on a relatively porous, thin, dense skin layer of the membrane comprises a hydrophilic polymer, a metal salt or a mixture of a metal salt and hydrogen peroxide, wherein said asymmetric integrally-skinned polymeric membrane comprises the relatively porous, thin, dense skin layer is characterized by a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure.

2. The stable high performance facilitated transport membrane of claim 1 wherein said metal salt comprises silver nitrate.

3. The stable high performance facilitated transport membrane of claim 1 comprising a polymer selected from a group consisting of a polyimide, a blend of two or more different polyimides, and a blend of a polyimide and a polyethersulfone.

4. The stable high performance facilitated transport membrane of claim 3 wherein the polyimide is selected from the group consisting of poly(2,2'-bis-(3,4-dicarboxyphenyl) hexafluoropropane dianhydride-3,3',5,5'-tetramethyl-4,4'-methylene dianiline) polyimide derived from a polycondensation reaction of 2,2'-bis-(3,4-dicarboxyphenyl) hexafluoropropane dianhydride (6FDA) with 3,3',5,5'-tetramethyl-4,4'-methylene dianiline (TMMDA), poly(3,3',4,4'-diphenylsulfone tetracarboxylic dianhydride-3,3',5,5'-tetramethyl-4,4'-methylene dianiline) polyimide derived from the polycondensation reaction of 3,3',4,4'-diphenylsulfone tetracarboxylic dianhydride (DSDA) with TMMDA, poly(3,3',4,4'-benzophenone tetracarboxylic dianhydride-pyromellitic dianhydride-3,3',5,5'-tetramethyl-4,4'-methylene dianiline) polyimide derived from the polycondensation reaction of a mixture of 3,3',4,4'-benzophenone tetracarboxylic dianhydride (BTDA) and pyromellitic dianhydride (PMDA) with TMMDA, poly(3,3',4,4'-benzophenone tetracarboxylic dianhydride-pyromellitic dianhydride-2,4,6-trimethyl-1,3-phenylenediamine) polyimide derived from the polycondensation reaction of a mixture of BTDA and PMDA with 2,4,6-trimethyl-1,3-phenylenediamine (TMPDA), poly(3,3',4,4'-benzophenone tetracarboxylic dianhydride-pyromellitic dianhydride-2,4,6-trimethyl-1,3-phenylenediamine-2,4-toluenediamine) polyimide derived from the polycondensation reaction of a mixture of BTDA and PMDA with a mixture of TMPDA and 2,4-toluenediamine (2,4-TDA), and poly(3,3',4,4'-diphenylsulfone tetracarboxylic dianhydride-3,3',5,5'-tetramethyl-4,4'-methylene dianiline-4,4'-diamino-2-methylazobenzene) polyimide derived from the polycondensation reaction of DSDA with a mixture of TMMDA and 4,4'-diamino-2-methylazobenzene (DAMAB).

5. A method of making a stable high performance facilitated transport membrane comprising an asymmetric integrally-skinned polymeric membrane wherein the method comprises:
   (a) preparing the asymmetric integrally-skinned polymeric membrane comprising a relatively porous, thin, dense skin layer and having a $CO_2$ permeance of at least 200 GPU and a $CO_2$ over $CH_4$ selectivity between 1.1 and 10 at 50° C. under 50-1000 psig, 10% $CO_2$/90% $CH_4$ mixed gas feed pressure;
   (b) preparing a hydrophilic polymer-nipped asymmetric integrally-skinned polymeric membrane by dripping an aqueous solution of a hydrophilic polymer with a concentration in a range of 50 ppm to 5000 ppm onto the surface of said asymmetric integrally-skinned polymeric membrane comprising the relatively porous, thin, dense skin layer prepared in step (a); and
   (c) preparing the facilitated transport membrane by soaking the relatively porous, thin, dense skin layer of said hydrophilic polymer-nipped asymmetric integrally-skinned polymeric membrane prepared in step (b) in an aqueous solution of a metal salt, or in an aqueous solution of a metal salt and hydrogen peroxide for a sufficient time to form the facilitated transport membrane wherein the relatively porous, thin, dense skin layer of the membrane comprises the metal salt, or a mixture of the metal salt and hydrogen peroxide.

6. The method of claim 5 wherein said metal salt is silver nitrate.

7. The method of claim 5 wherein said stable high performance facilitated transport membrane is in a form selected from the group consisting of hollow fibers, tubes and flat sheets.

8. The method of claim 5 wherein the stable high performance facilitated transport membrane is in a form of a flat sheet having a thickness from about 30 to about 400 µm.

9. The method of claim 5 wherein the stable high performance facilitated transport membrane is in a form of a hollow fiber module comprising from about 1,000 to 1,000,000 parallel, hollow fibers or tubes wherein each hollow fiber has an outside diameter of from about 200 micrometers (µm) to about 700 millimeters (mm) and a wall thickness of from about 30 to about 200 µm.

10. A process for the separation of paraffins and olefins, using a stable high performance facilitated transport membrane comprising an asymmetric integrally-skinned polymeric membrane wherein the pores on the relatively porous, thin, dense skin layer of the membrane comprises a hydrophilic polymer, a metal salt, or a mixture of a metal salt and hydrogen peroxide, the process comprising:

(a) providing the stable high performance facilitated transport membrane comprising the asymmetric integrally-skinned polymeric membrane wherein the pores on the relatively porous, thin, dense skin layer of the membrane comprises the hydrophilic polymer, the metal salt, or a mixture of the metal salt and hydrogen peroxide wherein said membrane is permeable to said olefins;

(b) contacting a humidified olefins/paraffins mixture feed on one side of said stable high performance facilitated transport membrane to cause said olefins to permeate the membrane; and (c) removing from the opposite side of said membrane a permeate gas composition comprising at least a portion of said olefins which permeated through said membrane.

11. The process of claim 10 wherein said olefins and paraffins are in a gaseous stream produced from stream cracking, catalytic cracking, or the dehydration of paraffins.

12. The process of claim 10 wherein said olefins comprise isobutylene, propylene or ethylene and said paraffins comprise isobutene, propane or ethane.

13. The process of claim 10 wherein said permeate gas composition has a concentration of olefin of 99.5 mass percent.

* * * * *